(12) United States Patent
Saifer et al.

(10) Patent No.: US 6,544,770 B2
(45) Date of Patent: Apr. 8, 2003

(54) QUANTITATION OF VIRUSES BY LIGHT SCATTERING

(75) Inventors: Mark G. P. Saifer, San Carlos, CA (US); L. David Williams, Fremont, CA (US)

(73) Assignee: Mountain View Pharmaceuticals, Inc., Menlo Park, CA (US)

( * ) Notice: Subject to any disclaimer, the term of this patent is extended or adjusted under 35 U.S.C. 154(b) by 0 days.

(21) Appl. No.: 09/969,264

(22) Filed: Sep. 24, 2001

(65) Prior Publication Data

US 2002/0028439 A1 Mar. 7, 2002

Related U.S. Application Data

(62) Division of application No. 09/408,290, filed on Sep. 29, 1999, now Pat. No. 6,316,185.

(51) Int. Cl.$^7$ .................................................. C12Q 1/70
(52) U.S. Cl. ...................... 435/235.1; 435/5; 435/239; 436/161; 436/171; 436/172; 356/337; 356/338; 356/339; 356/340
(58) Field of Search ....................... 435/5, 235.1, 239; 436/161, 171, 172; 356/337, 338, 339, 340

(56) References Cited

U.S. PATENT DOCUMENTS

| | | | |
|---|---|---|---|
| 4,884,886 A | 12/1989 | Salzman et al. | |
| 5,269,937 A | 12/1993 | Dollinger et al. | |
| 5,772,888 A | 6/1998 | Liu et al. | |
| 5,837,520 A | 11/1998 | Shabram et al. | |
| 6,316,185 B1 | * 11/2001 | Saifer et al. | |

OTHER PUBLICATIONS

Bistocchi, M. et al., *Tumori* 63:525–534, (1977).
Camerini–Otero, R.D., et al., *Biochemistry* 13:960–970, (1974).
Cummins, H.Z., et al., *Biophys. J.* 9:518–546, (1969).
Lago, P. et al., *Rev. Sci. Instrum.* 64:1797–1802, (1993).
Mittereder, N., et al., *J. Virol.* 70:7498–7509, (1996).
Samoylova, T.I., et al., *BioTechniques* 27:356–361, (1999).
Shabram, P.W., et al., *Hum. Gene Ther.* 8:453–465, (1997).
Smith, C.E., et al., *Biochemistry* 6:2457–2465, (1967).
Tikhonenko, T.I., et al., *Mol. Biol.* (Moscow) 12:393–395, (1978).
Tsoka, S., et al., *Biotechnol. Bioeng.* 63:290–297, (1999).

* cited by examiner

*Primary Examiner*—Leon B. Lankford, Jr.
(74) *Attorney, Agent, or Firm*—Knobbe, Martens, Olson & Bear LLP

(57) ABSTRACT

A method for determining the number or concentration of virus particles in a sample by use of a light scattering detector. The method may be used to quantitate purified virus preparations or virus samples containing contaminants, including ultraviolet light-absorbing contaminants, such as proteins. The method is useful for quantitation of viruses for use in gene therapy, oncolytic viruses for tumor cell lysis and virus-based vaccines.

8 Claims, 3 Drawing Sheets

Detection of 4.4 x $10^9$ Adenovirus Particles by Ion-Exchange Chromatography Using Light Scattering at 90° and Absorbance at 260 nm Comparison of Standard Curves for Quantitation of Adenovirus Detected by Light Scattering at 90° and by Absorbance at 260 nm Comparison of Sensitivities of Viral Detection by Light Scattering and Absorbance, with a 1000:1 Ratio of Voltage Scales

QUANTITATION OF VIRUSES BY LIGHT SCATTERING

This appln is a Div. of Ser. No. 09/408,290 filed Sep. 29, 1999 now U.S. Pat. No. 6,316,185.

FIELD OF THE INVENTION

The present invention relates to virus quantitation. More specifically, the invention relates to quantitation of viruses by measuring scattered light.

DESCRIPTION OF THE RELATED ART

Determination of virus concentration is important in, among other things, quantitation of viral vectors for use in gene therapy, quantitation of oncolytic viruses and quantitation of virus-based vaccine compositions. The quantitation of viruses for use in gene therapy with accuracy and precision is critical to ensure adequate comparability of data obtained in various intra-and inter-institutional studies, as well as to ensure comparability between virus preparations used for preclinical and clinical studies (Mittereder et al., *J. Virol.* 70:7498–7509, 1996). The quantitation of viruses that lyse tumor cells (oncolytic viruses) is also important in determining the correct dosage. In addition, quantitation of virus-based vaccines is important for safety and efficacy of administration of these compositions.

Examples of oncolytic viruses include mutated adenovirus (Heise et al., *Nat. Med.* 3:639–645, 1997), mutated vaccinia virus (Gnant et al., *Cancer Res.* 59:3396–3403, 1999) and mutated reovirus (Coffey et al., *Science* 282:1332–1334, 1998). Examples of viral vectors for use in gene therapy include mutated vaccinia virus (Lattime et al., *Semin. Oncol.* 23:88–100, 1996), mutated herpes simplex virus (Toda et al., *Hum. Gene Ther.* 9:2177–2185, 1998), mutated adenovirus (U.S. Pat. No. 5,698,443) and mutated retroviruses (Anderson, *Nature* 392(Suppl.):25–30, 1998).

As early as the 1960s and 1970s, light scattering measurements were used to study the assembly and aggregation of viral components and viral particles (Smith et al., *Biochemistry* 6:2457–2465, 1967; Cummins et al., *Biophys. J.* 9:518–546, 1969; Camerini-Otero et al., *Biochemistry* 13:960–970, 1974). Diffusion coefficients, molecular weights and particle dimensions of viruses and viral components have all been studied with light scattering techniques. These studies have emphasized the variation of light scattering per virus particle, depending on the state of aggregation, association, dissociation, etc., of the virus particles. Modern light scattering detectors are designed to permit characterization of the size distributions of molecules and particles, including viruses, using an auxiliary detector (e.g., ultraviolet light absorbance detector or refractive index detector) as the concentration detector.

U.S. Pat. No. 5,837,520 to Shabram et al. discloses and claims a method for determining the number of intact virus particles in a sample by monitoring the ultraviolet absorbance of the effluent from a column of an anion exchange resin and comparing that absorbance to a standard curve that is prepared with virus suspensions of known concentrations. This method, with measurement of light absorbance at 260 nm and 280 nm, is used by Shabram et al. (*Hum. Gene Ther.* 8:453–465, 1997) to quantitate adenovirus in suspensions.

Publications on light scattering in the context of virus quantitation emphasize the interference by light scattering with ultraviolet light absorbance measurements (Maizel et al., *Virology* 36:115–125, 1968; Tikhonenko et al., *Mol. Biol.* (Moscow) 12:393–395, 1978; Mittereder et al. supra). Tsoka et al. (*Biotechnol. Bioeng.* 63:290–297, 1999) use dynamic light scattering to detect distributions of particle sizes in suspensions of virus-like particles, and teach that it is necessary to add antibodies to a suspension of virus-like particles in order to induce a change in particle size that can then be measured by dynamic light scattering.

Dynamic light scattering measurements are distinct from static light scattering measurements. Typically, dynamic light scattering (also known as photon correlation spectroscopy) is an optical method used to study the Brownian motion of particles in solution. Measurements are taken to detect fluctuations in the intensity of light scattered by a sample, at time points on a scale related to the time taken for a particle to diffuse a distance comparable to the wavelength of the light scattered. See Tsoka et al. In contrast, static light scattering is not based on fluctuations in intensity over time, and is not directed to detecting Brownian motion or diffusion rates of particles.

Bistocchi et al (*Tumori* 63:525–534, 1977) describe quantitation of murine mammary tumor virus (muMTV) in mouse milk, and refer to their virus quantitation as having been done by "light scattering." However, this reference does not actually describe the use of a light scattering detector for quantitating viruses, but instead describes the measurement of ultraviolet light absorbance at 260 nm, which is also referred to by those authors as optical density. It is the increase in optical density (i.e. the decrease in transmitted light) that these authors refer to as "light scattering." Light absorbance and light scattering are distinct phenomena: the optical density values of the samples of Bistocchi et al. include contributions from light scattering by the virus particles (which decreases the amount of light transmitted through the sample), as well as contributions from light absorbance at 260 nm by milk proteins and by viral nucleic acids. The authors took into account the expected light absorbance by milk proteins, based on the protein content of the milk as determined by the method of Lowry et al. (*J. Biol. Chem.* 193:265–275, 1951). However, they apparently assumed that after correcting for the light absorbance due to milk proteins, the result would be a measure of light scattering by virus particles. They did not take into account the light absorbance at 260 nm due to viral nucleic acids. In any case, this reference does not actually report quantitation of a virus by light scattering, but instead reports quantitation of a virus by an adjusted or corrected ultraviolet light absorbance measurement.

An important difference between an absorbance measurement and a light scattering measurement is that the detector for measuring absorbance must be placed on the side of the sample opposite to the light source, along the axis of illumination, where it measures the decrease in light transmitted through the sample, as done by Bistocchi et al. On the other hand, a detector for measuring scattered light is placed away from the axis of illumination, for example at 90 degrees to that axis, to measure the increase in light that is scattered by the sample at a non-zero angle to the incident beam. A second difference between absorbance and scattering measurements stems from the necessity to employ a wavelength that is specifically absorbed by the sample in the former method (e.g. ultraviolet light with a wavelength of 260 or 280 nm), whereas wavelengths that are not absorbed by the sample are preferred in the latter method (e.g. visible light with a wavelength of 690 nm from a diode laser, 632.8 nm from a helium-neon laser or 488 nm from an argon-ion laser).

There is an ongoing need for more accurate methods for measuring virus concentrations, particularly for adenovirus, for which no widely accepted standard method is known. The present invention addresses this need.

SUMMARY OF THE INVENTION

The present invention provides a method for determining the number or concentration of virus particles in a sample, including the steps of: measuring the amount of light scattered by the virus particles; and comparing the amount of light scattered to one or more known light scattering values correlated with one or more known concentrations of the virus. The comparing step may include a standard light scattering curve including several data points, wherein the data points are based on the light scattering values and the concentrations of the virus. The method may further include the step of purifying the virus particles using a fractionation system prior to the measuring step. The fractionation system may include a chromatographic medium, such as, for example, an ion-exchange medium, a size-exclusion medium, an affinity medium, and the like. The fractionation system may include one or more components such as a chromatography column, a countercurrent distribution apparatus, a two-phase system, a gradient, or a centrifuge. The virus may be, for example, an adenovirus, human herpesvirus, human papilloma virus, adeno-associated virus, flavivirus, dengue virus, Japanese encephalitis virus, human T-cell lymphotrophic virus, hepatitis virus, human immunodeficiency virus (HIV), cytomegalovirus (CMV), Epstein-Barr virus, reovirus, vaccinia virus, parvovirus, feline leukemia virus, cauliflower mosaic virus and tomato bushy stunt virus.

In another embodiment, the invention provides a system for quantitation of virus particles including a light source adapted for directing light along a light path, a sample within the light path, a detector positioned to detect light scattered at an angle to the light path, and a recorder in communication with the detector, wherein the sample may include a quantity of particles of a virus, and wherein a portion of the light may be scattered from the path at the angle by the virus particles, and wherein the detector detects the light scattered at the angle to produce a signal that is a function of the quantity of virus particles, and wherein the signal may be communicated to the recorder and converted to a value indicating the quantity of the virus particles. The detector may be selected from the group consisting of a multi-angle detector, a dual-angle detector, and a single-angle detector. The system may further include a fractionation system in communication therewith, wherein the fractionation system receives a pre-sample including the virus particles and other components, and wherein the fractionation system separates the virus particles from the other components. The virus may be, for example, an adenovirus, human herpesvirus, human papilloma virus, adeno-associated virus, flavivirus, dengue virus, Japanese encephalitis virus, human T-cell lymphotrophic virus, hepatitis virus, human immunodeficiency virus (HIV), cytomegalovirus (CMV), Epstein-Barr virus, reovirus, vaccinia virus, parvovirus, feline leukemia virus, cauliflower mosaic virus and tomato bushy stunt virus. The quantity measured by the system of this aspect of the invention may be a concentration of virus particles per unit volume of a liquid sample. For example, such concentration may be between about $10^8$ and $10^{12}$ virus particles/mL. Likewise, the quantity measured by the system of this aspect of the invention may be a number of virus particles in the sample. For example, such number maybe between about $10^8$ and $10^{10}$ virus particles.

DETAILED DESCRIPTION OF THE PREFERRED EMBODIMENTS

Figure 1:
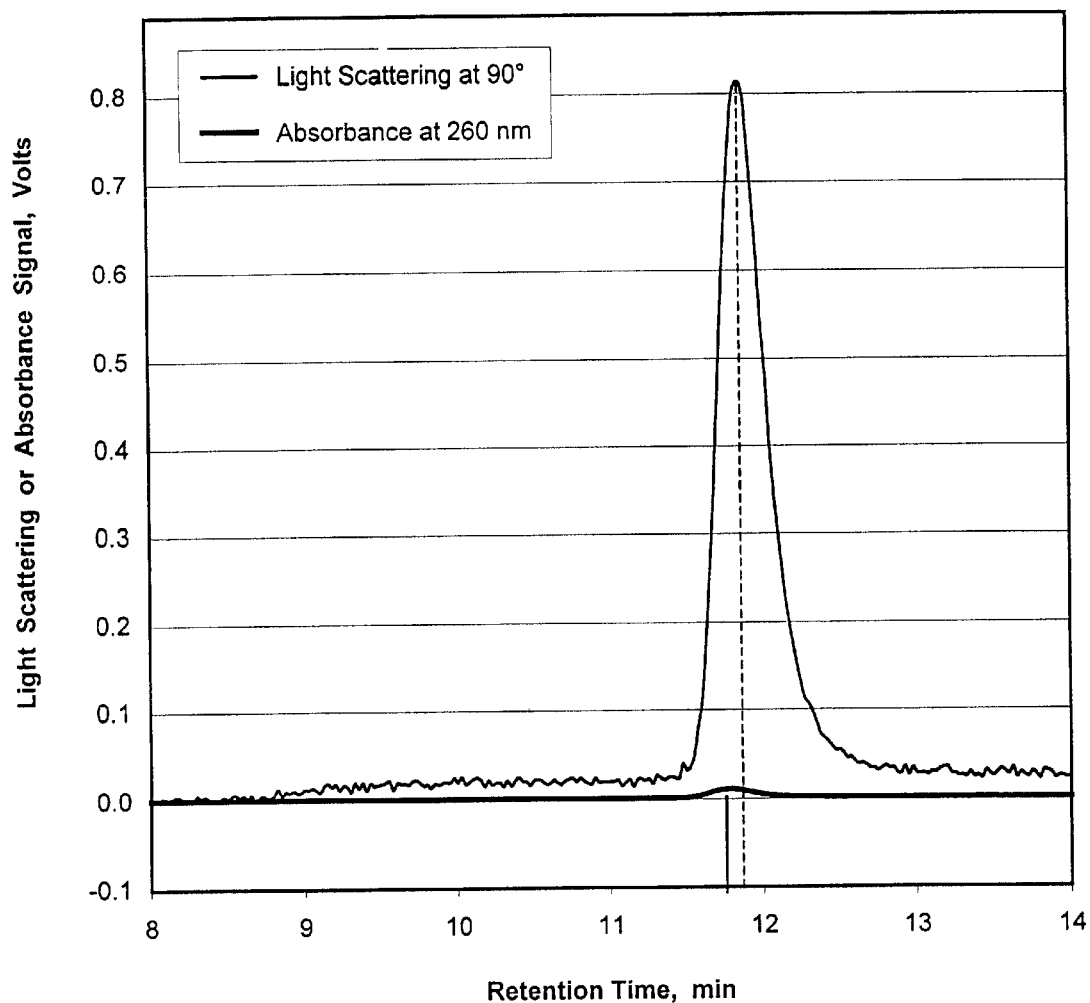
FIG. 1 is a graph showing detection of $4.4 \times 10^9$ adenovirus particles by ion-exchange chromatography using light scattering at 90° and absorbance at 260 nm.

The present invention includes the observation that the use of a light scattering detector as an alternative to an ultraviolet absorbance detector confers an unexpected increase in sensitivity and specificity of virus quantitation. Suitable light scattering detectors for use with this invention are multi-angle laser light scattering detectors (e.g. DAWN DSP or MiniDAWN detectors manufactured by Wyatt Technology Corp. of Santa Barbara, Calif.), dual-angle light scattering detectors or single-angle light scattering detectors, as illustrated in Examples 1 through 6.

This method can be used to quantitate any virus for which a suspension of homogeneous, purified virus particles is available at a known concentration, permitting calibration of the light scattering measurements with dilutions of the standardized suspension of that virus. In a preferred embodiment, virus particles are purified using any conventional fractionation system, such as a system that includes a chromatographic column. The chromatographic column may contain an ion-exchange medium (cationic or anionic), a size-exclusion medium, an affinity resin, or any other medium or resin capable of removing, retaining or retarding the movement of contaminants (molecules other than the virus particles of interest) so that virus particles are present in a substantially purified form in at least a portion of the column effluent. Many types of suitable separation media are available from many commercial sources, including Amersham-Pharmacia Biotech (Piscataway, N.J.), Sigma Chemical Co. (St. Louis, Mo.) and Bio-Rad Laboratories (Hercules, Calif.). The fractionation system may also include a two-phase system comprising aqueous solutions of dextran and poly(ethylene glycol), with or without a countercurrent distribution apparatus to facilitate separation of the two phases, a zonal or continuous-flow centrifuge, an ultracentrifuge employing, for example, density gradients, whether continuous or step gradients, and, additionally or alternatively, the fractionation system may include one or more size-selective membranes with appropriate molecular weight limits to separate the virus particles from accompanying molecules or cell debris, or both.

In a preferred embodiment, the fractionation system binds non-viral components and the virus particles appear in the eluate. In an alternative embodiment, the virus particles are retained in the column and the contaminants appear in the eluate. This is accomplished, for example, by using an affinity adsorbent to which an antibody having affinity for a viral surface protein is bound. The bound virus is then eluted using, for example, a peptide that competes with the virus for binding to the adsorbent.

Although the quantitation of purified virus preparations is preferred, the present method can also be used to quantitate virus without chromatographic separation, as demonstrated by the independence of the measurement of virus concentration on the concentration of contaminating bovine or human serum albumin, even when the contaminating protein represents more that 75%, 90%, 95%, or 99% of the protein present in the virus suspension. Light scattering can also be used to measure virus concentrations in virus suspensions containing polymers including, but not limited to, poly(ethylene)glycol and dextran. For accurate quantitation of virus particles by light scattering measurements in the presence of polymers, such polymers must not be sufficiently concentrated that they induce aggregation of the virus particles.

The present method may be used to quantitate viral vectors for use in gene therapy applications such as adenovirus and herpesviruses, for quantitation of oncolytic viruses such as ONYX-015 (U.S. Pat. Nos. 5,677,178 and 5,846,945), and for quantitation of virus-based vaccines, such as those for poliovirus, varicella-zoster virus, measles virus, and the like.

Although the use of light scattering for quantitation of adenovirus is described herein, this method may be used to quantitate any desired virus present in a sample including, for example, adeno-associated virus, human herpesvirus, human papilloma virus, pathogenic human flaviviruses such as dengue virus and Japanese encephalitis virus, human T-cell lymphotrophic viruses (HTLV-I and HTLV-II), hepatitis viruses A, B and C; human immunodeficiency viruses (HIV-1 and HIV-2), cytomegalovirus (CMV), Epstein-Barr virus (EBV), reovirus, vaccinia virus, canine parvovirus, feline leukemia virus, plant viruses such as cauliflower mosaic virus and tomato bushy stunt virus (TBSV), and the like. Viruses may be naturally occurring, genetically engineered, or otherwise modified; likewise the viruses may be virulent, attenuated, tropism-restricted, or killed, depending on the intended use thereof. Further, some embodiments of the present invention are likewise suitable for quantitation of virus-like particles as well as virus particles.

Static light scattering measurements thus offer high sensitivity of virus detection, and precision of quantitation across a wide range of virus particle concentration or absolute numbers of virus particles. These ranges may vary depending on the nature of the light scattering system and other software, hardware, or devices used in connection with the light scattering detector. For example, such concentration may be between about $10^8$ and $10^{12}$ virus particles/mL. Likewise, the quantity measured by the system of this aspect of the invention may be a number of virus particles in the sample. For example, such number maybe between about $10^8$ and $10^{10}$ virus particles.

EXAMPLE 1

Determination of Adenovirus Concentration by Light Scattering

Portions of a suspension of adenovirus (ONYX-015, Onyx Pharmaceuticals, Richmond, Calif.) containing 1.1×$10^{12}$ particles/mL were diluted 5-, 10- or 20-fold. Injections of 10, 20 or 40 μL were chromatographed on a 1-mL Resource Q anion-exchange column (Amersham-Pharmacia Biotech, Piscataway, N.J.), essentially as described in U.S. Pat. No. 5,837,520, the entire contents of which are hereby incorporated by reference, except that the effluent from the UV2000 ultraviolet light absorbance detector (Thermo Separation Products, San Jose, Calif.), which was programmed to measure absorbances at 260 nm and at 280 nm, was connected to a multi-angle light scattering detector with a 690-nm laser light source (MiniDAWN, Wyatt Technology Corp., Santa Barbara, Calif.). The 0- to 10-volt output from the MiniDAWN photodiode at 90 degrees to the incident light beam was split 1/11 and used as auxiliary detector input for the SP4500 Data Interface Module (0- to 1-volt A/D converter, Thermo Separation Products). The voltage signals from both the ultraviolet absorbance detector and the static light scattering detector were communicated to and recorded by a personal computer and integrated by SP1000 software (Thermo Separation Products) to obtain peak areas in units of millivolt-seconds (mV-sec). The ratio of the integrated absorbance peak at 260 nm to the integrated absorbance peak at 280 nm for the virus peak was consistently found to be approximately 1.2:1. Since the absorbance at 260 nm was consistently proportional to and higher than that at 280 nm, the signal from the light scattering detector is compared to only the larger of these two absorbance signals in the results summarized in Table 1.

TABLE 1

| Virus dilution | Volume injected μL | Virus particles injected × $10^{-9}$ | Integrated light scattering signal mV-sec | Integrated 260 nm absorbance signal mV-sec | Ratio of light scattering to 260 nm absorbance |
|---|---|---|---|---|---|
| 1/20 | 10 | 0.55 | 2,510 | 33.4 | 75 |
| 1/10 | 10 | 1.1 | 4,440 | 59.3 | 75 |
| 1/20 | 20 | 1.1 | 4,530 | 60.0 | 76 |
| 1/5 | 10 | 2.2 | 9,420 | 123 | 76 |
| 1/10 | 20 | 2.2 | 9,060 | 117 | 77 |
| 1/20 | 40 | 2.2 | 9,090 | 123 | 74 |
| 1/5 | 20 | 4.4 | 18,980 | 239 | 80 |
| 1/10 | 40 | 4.4 | 19,540 | 241 | 81 |

Figure 2:
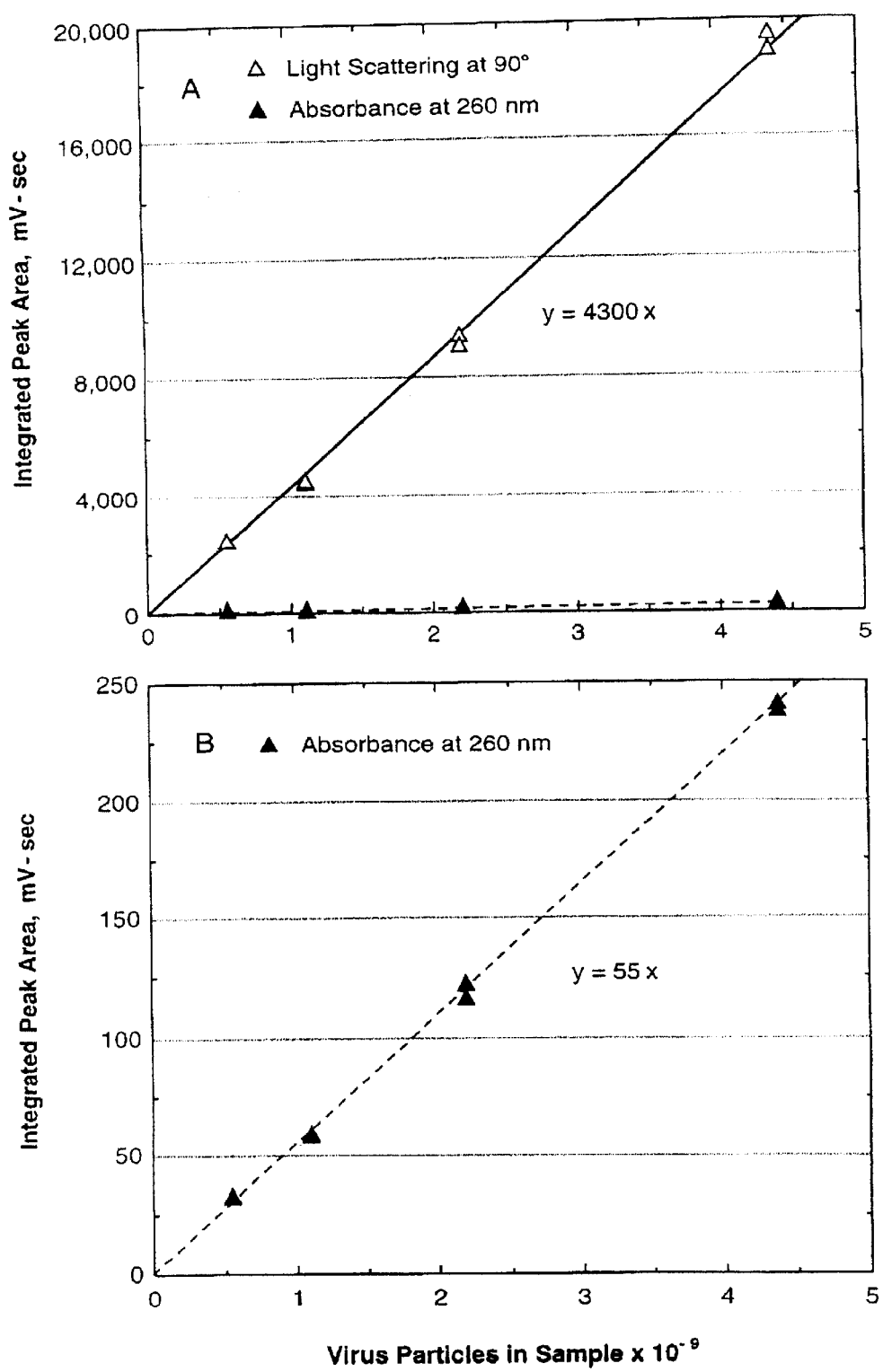
FIG. 2A is a graph showing standard curves for quantitation of adenovirus detected by light scattering at 90° and by absorbance at 260 nm.
FIG. 2B is a graph showing a standard curve for quantitation of adenovirus detected by absorbance at 260 nm, on an expanded scale relative to FIG. 2A.

FIG. 1 illustrates the results obtained for a 20 μL injection of a 1/5 dilution of ONYX-015 (4.4×$10^9$ particles). The difference in retention times for the absorbance peak and the light scattering peak results from the volume of the capillary tubing between the two detectors, which is approximately 0.125 mL (corresponding to 0.125 minutes at 1.0 mL/min). FIG. 2A compares the standard curves for the integrated light scattering signal and the integrated absorbance signal at 260 nm. FIG. 2B shows the same data for the absorbance signal on an 80-fold expanded scale.

Measurements by both detection systems were linearly related to the number of particles injected and independent of the volume of diluted sample that was injected within the tested range of 5.5×$10^8$ to 4.4×$10^9$ particles and the range of 10 to 40 μL, as shown in Table 1. Results obtained with the two detection systems differed primarily in that the attenuated voltage signal from the light scattering detector was more than 70-fold greater than the voltage signal from the ultraviolet absorbance detector.

EXAMPLE 2

Comparison of Light Scattering at a Right Angle and a Larger Angle

Proceeding as described in Example 1, light scattering signals were collected at 90 and 138.5 degrees to the incident laser beam of a MiniDAWN light scattering detector with a 690-nm laser light source. The 0- to 10-volt outputs from the photodiodes of the MiniDAWN were collected by a personal computer using Astra software-provided by Wyatt Technology Corp. (Santa Barbara, Calif.). The 0- to 2-volt output from the 260-nm ultraviolet light absorbance detector was collected by a personal computer using SP1000 software of the chromatography workstation (Thermo Separation Products) and the data from both data acquisition systems were combined in an Excel workbook (Microsoft Corporation, Seattle, Wash.). The results in FIG. 3 were obtained from a sample containing $5.5\times10^8$ adenovirus particles. For ease of comparison of the results from the two light scattering detectors and the absorbance detector, 3 volts were subtracted from the light scattering signal from the photodiode at 138.5 degrees and the ultraviolet absorbance signal was plotted on a 1,000-fold expanded scale. In addition, the time scale for the light scattering signals was corrected for a delay of 0.125 minutes relative to the absorbance data (cf FIG. 1).

Figure 3:
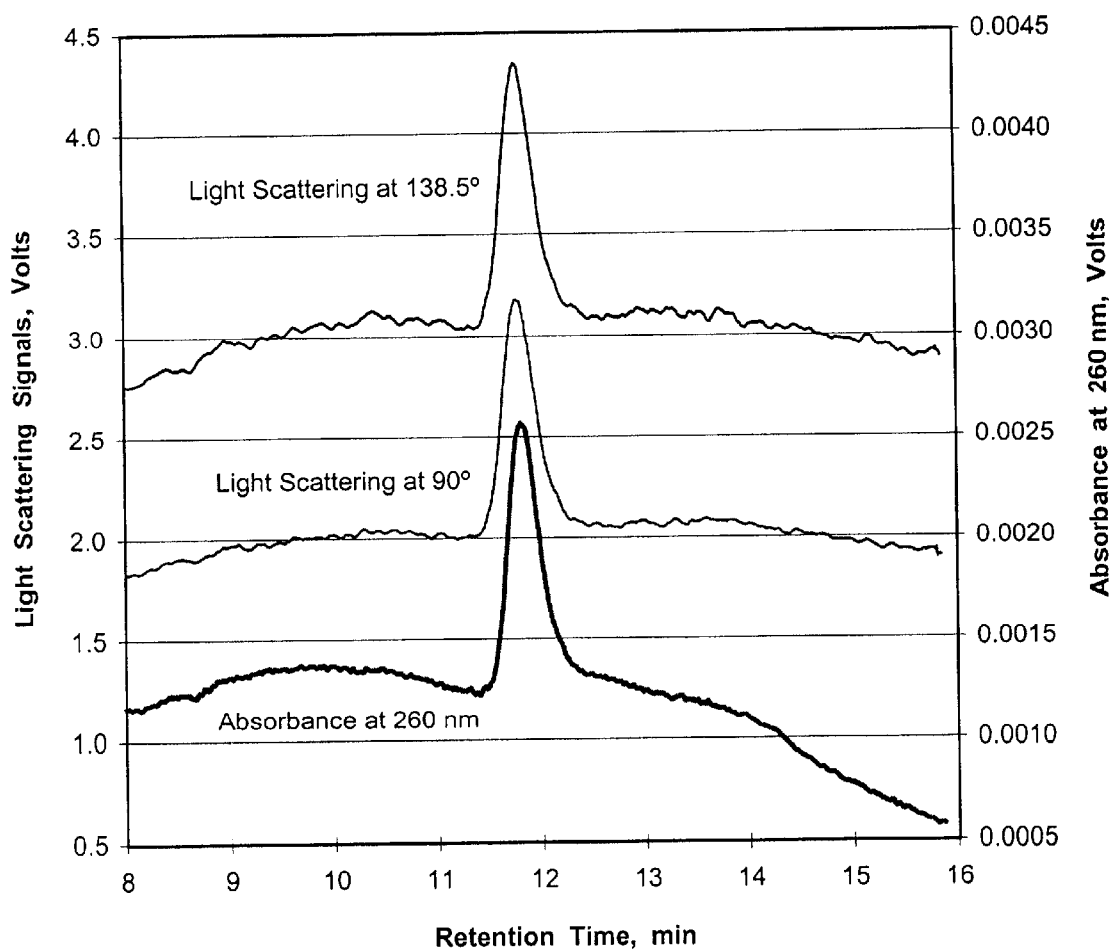
FIG. 3 is a graph showing light scattering at two angles and absorbance measured at 260 nm for quantitation of $5.5 \times 10^8$ adenovirus particles.

It is apparent from FIG. 3 that the peak heights and baseline fluctuations are similar for light scattering measured at 90 and at 138.5 degrees and that the baseline of the absorbance signal varies far more than do the baselines of the light scattering signals. The signal-to-noise ratio of the light scattering method in this example is superior to that of the method described in Example 1. It is also apparent that this small quantity of virus ($5.5\times10^8$ adenovirus particles) gives a peak height of more than one volt (i.e. 12% or 13% of the 10-volt dynamic range of the light scattering detectors), whereas the same quantity of virus gives an absorbance peak height of slightly more than one thousandth of a volt (1 mV), which is less than 0.1% of the 2-volt dynamic range of the absorbance detector. That a quantity of virus that produces an absorbance peak of only 0.0013 absorbance units (optical density units at 260 nm) at its maximum can yield a light scattering signal of more than 10% of full scale is truly unexpected.

EXAMPLE 3

Sensitivity and Detection Limits

Portions of a suspension of adenovirus (ONYX-015, Onyx Pharmaceuticals, Richmond, Calif.) containing $11.8\times10^{10}$ particles/mL were serially diluted 2-fold through 128-fold to produce virus suspensions that ranged in concentration from $9.2\times10^8$ particles/mL to $11.8\times10^{10}$ virus particles/mL (the undiluted sample). injections of 50 µL of suspending buffer and of each dilution were chromatographed on a 1-mL Resource Q anion-exchange column (Amersham-Pharmacia Biotech, Piscataway, N.J.), essentially as described in Example 1. Proceeding as described in Example 1, light scattering signals were collected at 90 degrees to the incident laser beam of a MiniDAWN light scattering detector with a 690-nm laser light source. The 0- to 10-volt output from the photodiode of the MiniDAWN and the 0- to 2-volt output from the 260-nm ultraviolet light absorbance detector were communicated to and recorded by a personal computer using Astra 4.00 software provided by Wyatt Technology Corp. (Santa Barbara, Calif.). With this data acquisition system, a peak with the retention time of the virus was detected by light scattering in all of the dilutions of virus ($9.2\times10^8$ to $11.8\times10^{10}$ particles/mL, containing $4.6\times10^7$ to $5.9\times10^9$ virus particles in the 50-µL samples). In contrast, no discernable peak was seen by Astra analysis of the ultraviolet absorbance signals in samples containing fewer than $7.4\times10^8$ virus particles, i.e. in the last four dilutions.

In accordance with a November 1996 recommendation of the International Conference on Harmonization of Technical Requirements for Registration of Pharmaceuticals for Human Use (ICH, Geneva, Switzerland), the Limit of Detection (LOD) and Limit of Quantitation (LOQ) of a calibration curve are given, respectively, by 3.3 times and 10 times the ratio of the standard deviation of the response noise to its slope. In addition, the ICH defines the sensitivity of a test method as the slope of the calibration curve. According to these definitions, the LOD and LOQ of the light scattering signal were calculated to be $0.8\times10^8$ and $2.6\times10^8$ virus particles, respectively. The detection limits were found to be several times higher for the absorbance measurements than for the light scattering measurements and the sensitivity of the light scattering method was found, in this example, to be approximately 3,000 times that of the absorbance method, based on a peak height of 119 mV per $10^8$ virus particles by light scattering (correlation coefficient, $R^2=0.995$) compared with a peak height of 0.039 mV per $10^8$ particles by absorbance at 260 nm ($R^2=0.982$). While the Astra software is not well suited for quantitation of detector signals below 1 mV, the use of other data analysis applications and/or other devices, such as for output signal amplification, is within the scope of the present invention, as would be appreciated by those of skill in the art.

EXAMPLE 4

Determination of the Concentration of Purified Adenovirns

The concentration of a suspension of purified adenovirus in Tris-buffered saline (pH 7.4) containing 1 mM $MgCl_2$ is measured by determining the intensity of scattered light after injecting approximately 0.9 mL of the suspension into the flow-cell of a MiniDAWN light scattering detector that has been calibrated by injection of a series of dilutions of an adenovirus suspension of known concentration. The particle concentration that is measured in this batch mode is substantially equal to the particle concentration that is measured by the chromatographic methods described in Examples 1 and 2. An advantage of the method of this example, compared to measurement techniques that require disruption of the virus particles (e.g, the methods of Maizel et al. supra or Mittereder et al. supra), is that the present example employs a non-destructive test of the concentration of virus particles, permitting recovery of the virus suspension for further use. In addition, this batch method (which requires a larger sample volume than does a chromatographic method) can measure much lower concentrations of viruses than can be measured with a size-exclusion chromatographic method.

Example 5

Measurement of Adenovirus Concentration in Solution Containing Human Serum Albumin The concentration of a suspension of purified adenovirus in phosphate-buffered saline (PBS, pH 7.4) containing 1% (w/v) human serum albumin is measured by determining the intensity of scattered light after injecting 1–2 mL of the suspension into a MiniDAWN light scattering detector that has been calibrated by injection of a series of dilutions of an adenovirus suspension of known concentration. The particle concentration of this suspension could not be measured by protein assay (Bistocchi et al. supra) or by ultraviolet absorbance assay (Maizel et al. supra) because of the interference with those methods by the carrier protein; however, the intensity of light scattering is hardly influenced by the carrier protein and the particle concentration that is measured by this batch method is essentially the same as is obtained with a chromatographic method (e.g. based on size differences or charge differences) that separates the virus from the accompanying carrier protein before measuring the intensity of light scattering. Furthermore, the method of this example is more precise than a method for quantitation of virus particles that is based on the polymerase chain reaction (PCR).

EXAMPLE 6

Quantitation of Virus in a Partially Purified Virus Preparation

A partially-purified preparation of virus from a process employed in the manufacture of a vector for use in gene-therapy (e.g., adenovirus) is subjected to fractionation by zone centrifagation in a sucrose gradient. The contents of the gradient are caused to flow through a light-scattering detector that has been calibrated by injection of a series of dilutions of a virus suspension of known concentration. The intensity of scattered light in the region of the gradient that contains the virus, when compared to the calibration curve, indicates the distribution of the concentration of the virus particles. After collecting the virus-containing region of the density gradient, the concentration of virus particles in the product pool is determined by the method of Example 4.

It should be noted that the present invention is not limited to only those embodiments described in the Detailed Description. Any embodiment that retains the spirit of the present invention should be considered to be within its scope. The invention is only defined by the following claims.

What is claimed is:

1. A system for quantitation of virus particles comprising a light source adapted for directing light along a light path, a sample within said light path, a detector positioned to detect light scattered at an angle to said light path, and a recorder in communication with said detector, wherein said sample comprises a quantity of particles of a virus, and wherein a portion of said light is scattered from said path at said angle by said virus particles, and wherein said detector detects said light scattered at said angle to produce a signal that is a function of said quantity of virus particles, and wherein said signal is communicated to said recorder and converted to a value indicating said quantity of said virus particles.

2. The system of claim 1, wherein the detector is selected from the group consisting of a multi-angle detector, a dual-angle detector, and a single-angle detector.

3. The system of claim 1, further comprising a fractionation system in communication therewith, wherein said fractionation system receives a pre-sample comprising said virus particles and other components, and wherein said fractionation system separates said virus particles from said other components.

4. The system of claim 1, wherein said virus is selected from the group consisting of human herpesvirus, human papilloma virus, adeno-associated virus, flavivirus, dengue virus, Japanese encephalitis virus, human T-cell lymphotrophic virus, hepatitis virus, human immunodeficiency virus (HIV), cytomegalovirus (CMV), Epstein-Barr virus, reovirus, vaccinia virus, parvovirus, feline leukemia virus, cauliflower mosaic virus and tomato bushy stunt virus.

5. The system of claim 1, wherein said quantity is a concentration of virus particles per unit volume of a liquid sample.

6. The system of claim 5, wherein said concentration is between $10^8$ and $10^{12}$ particles/mL.

7. The system of claim 1, wherein said quantity is a number of virus particles in said sample.

8. The system of claim 7, wherein said number is between $10^8$ and $10^{10}$ particles.

* * * * *